United States Patent
Nakagoshi et al.

(10) Patent No.: US 8,537,000 B2
(45) Date of Patent: Sep. 17, 2013

(54) ANTI-DROWSING DEVICE AND ANTI-DROWSING METHOD

(75) Inventors: Akira Nakagoshi, Toyota (JP); Kenji Kimura, Toyota (JP); Bertin Rodolphe Okombi-Diba, Nagoya (JP)

(73) Assignee: Toyota Jidosha Kabushiki Kaisha, Toyota-shi (JP)

( * ) Notice: Subject to any disclaimer, the term of this patent is extended or adjusted under 35 U.S.C. 154(b) by 1071 days.

(21) Appl. No.: 12/524,431

(22) PCT Filed: Jan. 24, 2008

(86) PCT No.: PCT/IB2008/000150
§ 371 (c)(1),
(2), (4) Date: Jul. 24, 2009

(87) PCT Pub. No.: WO2008/090451
PCT Pub. Date: Jul. 31, 2008

(65) Prior Publication Data
US 2010/0214087 A1  Aug. 26, 2010

(30) Foreign Application Priority Data
Jan. 24, 2007  (JP) ................................ 2007-014135

(51) Int. Cl.
*G08B 1/08* (2006.01)
(52) U.S. Cl.
USPC ...... 340/539.13; 340/436; 340/435; 340/903; 340/425.5; 340/438; 340/573.1; 340/575; 340/576; 701/301
(58) Field of Classification Search
USPC .............. 340/435, 436, 901, 903, 425.5, 438, 340/573.1, 575, 576
See application file for complete search history.

(56) References Cited

U.S. PATENT DOCUMENTS

| | | |
|---|---|---|
| 2004/0070509 A1 | 4/2004 | Grace et al. |
| 2004/0090334 A1 | 5/2004 | Zhang et al. |
| 2006/0103539 A1* | 5/2006 | Isaji et al. ..................... 340/575 |
| 2009/0303078 A1* | 12/2009 | Mochizuki et al. ............ 340/901 |
| 2010/0253526 A1* | 10/2010 | Szczerba et al. ............... 340/576 |
| 2012/0179008 A1* | 7/2012 | Burton ......................... 600/301 |

FOREIGN PATENT DOCUMENTS

| | | |
|---|---|---|
| EP | 1 418 082 | 5/2004 |
| JP | 7 156682 | 6/1995 |
| JP | 8 147582 | 6/1996 |
| JP | 9 39603 | 2/1997 |
| JP | 2583335 | 2/1997 |
| JP | 9 293180 | 11/1997 |
| JP | 10 123262 | 5/1998 |
| JP | 11 78592 | 3/1999 |
| JP | 2003 16598 | 1/2003 |
| JP | 2004 145725 | 5/2004 |
| JP | 2004 216966 | 8/2004 |

* cited by examiner

Primary Examiner — Daryl Pope
(74) Attorney, Agent, or Firm — Oblon, Spivak, McClelland, Maier & Neustadt, L.L.P.

(57) ABSTRACT

An anti-drowsing device includes: an ECU that outputs a warning via a buzzer when a collision possibility between a preceding object and the vehicle is detected; a warning control ECU that establishes an early-warning mode in which a warning is output earlier from that used in a normal mode; and a driver monitor camera and a driver monitor ECU that monitors a driver's eyes. The warning control ECU establishes the early-warning mode when the eye-closing period of the driver becomes equal to or greater than a first threshold value, and thereafter maintains the early-warning mode until the eye-closing period of the driver falls below a second threshold value.

12 Claims, 11 Drawing Sheets

|  | DROWSINESS LEVEL | NUMBER OF SAMPLES | NUMBER OF SAMPLE CASES CLASSIFIED CORRECTLY | ACCURACY [%] |
|---|---|---|---|---|
| THIS EMBODIMENT ($\Delta Tw=30$ sec) | D0~D2 | 598 | 527 | 88.13 |
|  | D3~D4 | 881 | 659 | 74.8 |
| THIS EMBODIMENT ($\Delta Tw=10$ sec) | D0~D2 | 598 | 574 | 95.99 |
|  | D3~D4 | 881 | 598 | 67.88 |
| COMPARATIVE EXAMPLE 1 | D0~D2 | 598 | 554 | 92.64 |
|  | D3~D4 | 881 | 451 | 51.19 |
| COMPARATIVE EXAMPLE 2 (PERCLOS) | D0~D2 | 598 | 592 | 99 |
|  | D3~D4 | 881 | 431 | 48.92 |

ANTI-DROWSING DEVICE AND ANTI-DROWSING METHOD

BACKGROUND OF THE INVENTION

1. Field of the Invention

The present invention relates to an anti-drowsing device that changes the timing of output of a warning which is output when a collision possibility between an object ahead of a vehicle and the vehicle is detected, and a method therefor.

2. Description of the Related Art

A preceding vehicle proximity warning device is known having a host vehicle speed detection means for detecting the traveling speed of a host vehicle; a preceding vehicle speed detection means for detecting the traveling speed of a preceding vehicle; inter-vehicular distance detection means for detecting the following distance between the host vehicle and the preceding vehicle; a warning generation means for providing a warning to the driver when the speed of the host vehicle relative to the preceding vehicle becomes equal to or higher than a predetermined allowable relative speed depending on the following distance; and a driving state detection means for detecting inattentive driving or drowsy driving of the driver, in which the allowable relative speed is corrected to a lower value when inattentive driving or drowsy driving is detected, so that a warning is provided when the relative speed becomes equal to or higher than the corrected allowable relative speed (for example, see Japanese Patent No. 2583335 (JP-B-2583335)). According to the invention described in Japanese Patent No. 2583335 (JP-B-2583335), when drowsy driving is detected, the allowable relative speed is corrected to a lower value to establish an early-warning mode in which the timing of output of a warning is advanced from that used in a normal mode.

In the invention described in Japanese Patent No. 2583335 (JP-B-2583335), an inattentive state and a drowsy state are dealt with on the same basis, and an early-warning mode is established when an inattentive state or a drowsy state is detected. After that, if the inattentive state or the drowsy state is not detected any longer, the early-warning mode is immediately canceled and the operation is returned to the normal mode.

However, an inattentive state and a drowsy state have naturally different characteristics, and there may be a situation in which the driver is still feeling drowsy and the early-warning mode should be maintained even if a drowsy state is not detected any longer. That is, in general, after a drowsy state has been once detected, the driver may be struggling to keep his or her eyes open against heavy drowsiness even if a drowsy state is not detected any longer. It is therefore desirable to change the timing of output of a warning properly in view of the above point. On the other hand, when the early-warning mode is maintained for a long period after a drowsy state has once been detected, a warning may be output unnecessarily early and disturb the driver.

SUMMARY OF THE INVENTION

The present invention provides an anti-drowsing device that changes the timing of output of a warning which is output, when a collision possibility is detected between a preceding object and the vehicle, and a method therefor.

An anti-drowsing device according to a first aspect of the present invention has a warning output means that outputs a warning when a collision possibility is detected between a preceding object and the vehicle; a warning timing change means that establishes an early-warning mode in which the timing of output of a warning by the warning output means is advanced from that used in a normal mode; and an eye-closing period measurement means that monitors the state of the driver's eyes and measuring the period during which the driver's eyes are closed. The warning timing change means establishes the early-warning mode when the eye-closing period measured by the eye-closing period measurement means becomes equal to or greater than a first threshold value, and maintains the early-warning mode until the eye-closing period measured by the eye-closing period measurement means every time the driver's eyes are closed thereafter (hereinafter referred to as "subsequent eye-closing period") falls below a second threshold value which is smaller than the first threshold value.

The subsequent eye-closing period may be the maximum value of the eye-closing period measured by the eye-closing period measurement means within a predetermined period.

The predetermined period may be variable, and the predetermined period used when the vehicle is traveling on an expressway may be longer than the predetermined period used when the vehicle is running on an ordinary road.

A second aspect of the present invention relates to an anti-drowsing method for changing in which the timing of output of a warning, which is output when a collision possibility is detected between a preceding object and the vehicle. The anti-drowsing method has: a first index outputting step of monitoring the state of the driver's eyes and outputting a first index value that provides a temporal indication of the degree of the driver's drowsiness; a step of setting a first threshold value for the first index value; a step of establishing an early-warning mode in which the timing of output of a warning is advanced from that used in a normal mode when the first index value exceeds the first threshold value output in the first index outputting step; a second index value outputting step of monitoring the state of the eyes of the driver and outputting a second index value that provides a temporal indication of the degree of the driver's drowsiness after the step of establishing the early-warning mode; a step of setting a threshold value with which a lower drowsiness level can be detected than with the first threshold value for the second index value as a second threshold value; and the step of maintaining the early-warning mode until the second index value output in the second index value outputting step falls below the second threshold value.

The first index value may be one of the eye-closing period, the summation of the eye-closing periods over a predetermined period between the current time and a predetermined time before the current time, the ratio of the summation to the predetermined period, and the number of times the eye-closing period exceeds a predetermined threshold value within a predetermined period between the current time and a predetermined time before the current time.

The second index value may be one of the eye-closing period, the summation of the eye-closing periods over a predetermined period between the current time and a predetermined time before the current time, the ratio of the summation to the predetermined period, and the number of times the eye-closing period exceeds a predetermined threshold value within a predetermined period between the current time and a predetermined time before the current time.

According to the present invention, there can be obtained an anti-drowsing device which can properly change the timing of output of a warning which is output when a collision possibility is detected between a preceding object and the vehicle, and a method therefor.

BRIEF DESCRIPTION OF THE DRAWINGS

The foregoing and further features and advantages of the invention will become apparent from the following descrip

DETAILED DESCRIPTION OF THE EMBODIMENTS

Description is hereinafter made of an embodiment for implementing the present invention with reference to the drawings.

Figure 1:
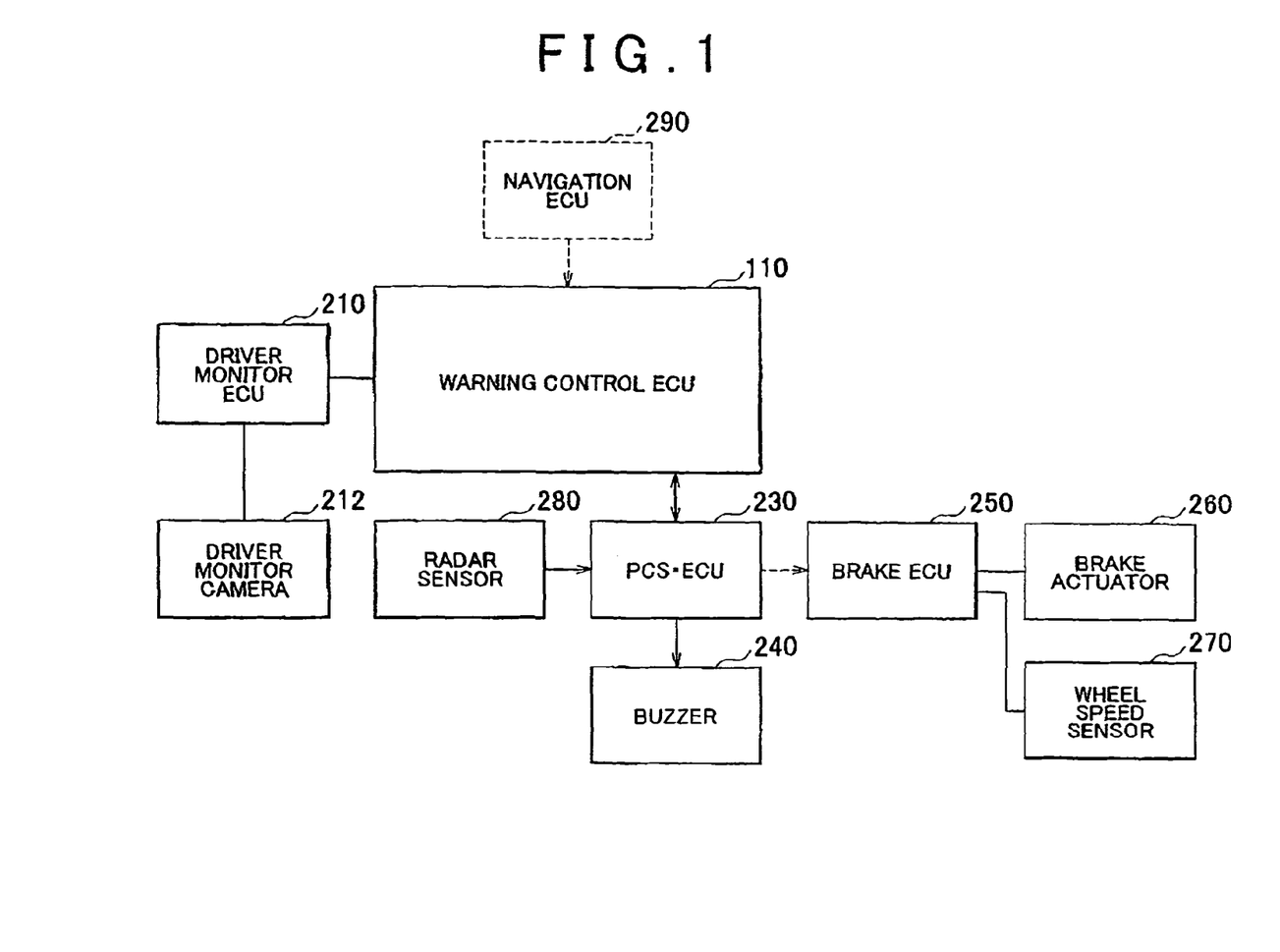
- FIG. 1 is a schematic diagram showing the main components of a warning system including an anti-drowsing device according to one embodiment of the present invention.

FIG. 1 is a schematic diagram showing the main components of a warning system that includes an anti-drowsing device according to one embodiment of the present invention. The anti-drowsing device of this embodiment includes a warning control ECU 110, a driver monitor ECU 210, a driver monitor camera 212, a PCS (pre-crash safety) ECU 230, and a buzzer 240.

The warning control ECU 110 has a hardware configuration centered on an appropriate processor or microcomputer and has a CPU that executes the operations described below, a ROM for storing programs and data that are sued in the operations, a readable and writable RAM for storing results of operations and the like, a timer, a counter, an input interface, an output interface and so on. While the other ECUs 210 and 230 may have the same or similar hardware configuration, it is needless to say that the programs and data (software configuration) stored in the ROM are different depending on the operations to be performed.

The driver monitor ECU 210 is connected to the warning control ECU 110 via an appropriate bus, and the driver monitor camera 212 is connected to the driver monitor ECU 210. The PCS ECU 230 is connected to the warning control ECU 110 via a bus in conformity with CAN (controller area network), and a radar sensor 280 and the buzzer 240 are connected to the PCS ECU 230. A brake ECU 250 may be connected to the PCS ECU 230 via a bus in conformity with CAN, for example. In this case, a brake actuator 260 and a wheel-speed sensor 270 are connected to the brake ECU 250. These connections are not necessarily made by wired connections, and some or all of the connections may be made by wireless connections. While the ECUs 110, 210 and 230 are described as separate units, some or all of the functions of an ECU may be implemented by another ECU or some of the functions of an ECU may be implemented by an additional ECU.

The radar sensor 280 is disposed near the radiator grill or in the front bumper of a vehicle to monitor objects that may be present ahead of the host vehicle. The radar sensor 280 emits detection waves and receives a reflected wave from an object ahead of the host vehicle (typically, a preceding vehicle) in the detection zone of the radar sensor 280 to determine the distance between the host vehicle to the object ahead of the host vehicle (hereinafter "preceding object") and the direction of the object relative to the host vehicle. Examples of the detection waves, which the radar sensor 280 emits, include light waves (for example, laser waves), radio waves (for example, millimeter waves), and sound waves (for example, ultrasonic waves). In addition, a plurality of radar sensors 280 may be provided to monitor the rear and/or both sides of the vehicle. Imaging sensors may be used instead of or in addition to the radar sensors 280 to monitor the front and/or the rear and/or both sides of the vehicle.

The PCS ECU 230 monitors the relative relation between the preceding object and the host vehicle based on the information of the object obtained from the radar sensor 280 every predetermined period and detects a collision possibility between the object and the host vehicle. In this embodiment, the PCS ECU 230 calculates and monitors an inter-vehicular time between the preceding object and the host vehicle based on the information of the object obtained from the radar sensor 280 every predetermined period, and detects a collision possibility between the preceding object and the host vehicle when the calculated inter-vehicular time is shorter than a predetermined threshold value Th (hereinafter referred to as "pre-crash determination threshold value"). The inter-vehicular time herein is the period from the current time to the predicted collision time, the time when a collision between the preceding object and the host vehicle is expected to occur, and is calculated by simply dividing the distance between the object and the host vehicle by the speed of the host vehicle relative to the object. In the normal mode (that is, not in an early-warning mode, which is described below), a default value T0 is used as the pre-crash determination threshold value Th. The default value T0 is set to a value in such a time range that a warning can be output sufficiently long before the predicted collision time to avoid the collision. That is, the default value T0 is set to a value in such a time range that a warning is effective. For example, the time range may be longer than the time range from the time at which a collision is unavoidable ("collision-unavoidable time") to the predicted collision time. This manner of setting the default value T0 is suitable to a constitution in which the brake ECU 250 performs forcible emergency braking or an automatic steering mechanism (not shown) performs collision-avoidance steering when a collision unavoidable state is detected. This is because outputting a warning after a collision unavoidable state is detected is of almost no importance since a collision avoidance action of the driver is useless even if the driver is warned that the collision is unavoidable. The default value T0 may be equal to the period from the collision unavoidable time to the predicted collision time.

Some other conditions may be added to the condition for detection of a collision possibility. For example, the fact that the angle formed by the speed vectors of the preceding object and the host vehicle is smaller than a predetermined angle, the fact that the amount of lateral offset between the preceding object and the host vehicle (the relative distance in a direction perpendicular to the traveling direction of the host vehicle) is within a predetermined value, the fact that the speed of the vehicle is equal to or higher than a predetermined value and so on may be added as the other conditions.

When a collision possibility between a preceding object and the host vehicle is detected, the PCS ECU 230 may output a collision warning via the buzzer 240. The method of outputting a collision warning is not limited to sound and may include vibrating a vibrator embedded in the seat or steering wheel, giving a thermal stimulation from a temperature changing means (for example, heater or Peltier element) embedded in the seat or steering wheel, causing the air conditioner to blow out a large amount of air suddenly, emitting light to the driver automatically to alert him or her, or allowing the brake ECU 250 to drive the brake actuator 260 to brake the vehicle forcibly in order to alert the driver. While outputting the collision warning, the PCS ECU 230 sends a signal informing the fact that the collision warning is outputting to the warning control ECU 110. The warning control ECU 110 can therefore keep track of the current output state (ON or OFF state) of the collision warning.

The driver monitor camera 212 may include a color or infrared-sensitive CCD (charge-coupled device) sensor array, for example. The driver monitor camera 212 is located in a position where it can capture the front side of the driver (the face of the driver from the front side thereof, for example). For example, the driver monitor camera 212 may be disposed on the dashboard of the instrument panel, steering column, rearview mirror or the like. The driver monitor camera 212 captures an image of the driver's face (hereinafter referred to as "face image") in real time. Typically, the driver monitor camera 212 sends the face image to the driver monitor ECU 210 in a 30 fps (frame per second) stream.

The driver monitor ECU 210 performs image processing on the face image continuously input from the driver monitor camera 212 and determines whether the driver's eyes are closed based on how far the eyelids of the driver are open (eyelid opening). There are various methods for determining whether the driver's eyes are closed based on image processing, and any appropriate method can be used. For example, affine transformation or the like is performed on the face image to correct the direction and size of the face, and, after an edge treatment, a matching procedure is performed on the parts of the face (mouth, nose, eyes) to identify the parts. Next, the maximum distance between the upper and lower eyelids (eyelid opening) is obtained based on feature quantities of parts of the eyes, the coordinate rows of the boundaries of the eyelids in this embodiment. Then, when the eyelid opening is smaller than a predetermined criterion value, it is determined that the driver's eyes are closed. In this case, a predetermined criterion value suitable for the driver is selected. That is, a predetermined criterion value is obtained in advance by sensory evaluation and stored in a database for each driver. The driver monitor ECU 210 performs the above determination on each image frame or on each image frame in a series of image frames (every certain period with a resolution finer than a normal blinking period), and sends the result of determination to the warning control ECU 110 at each determination period $\Delta T$. In this embodiment, in each determination period in which the driver's eyes are determined to be closed, the driver monitor ECU 210 sends a trigger signal indicating that the driver's eyes are closed (hereinafter referred to as "eye-closure trigger") to the warning control ECU 110.

A characteristic configuration of the warning control ECU 110 of this embodiment is next described.

The warning control ECU 110 calculates the eye-closing period d [sec], the period for which the eyes of the driver are closed, in real time based on the eye-closure trigger continuously input from the driver monitor ECU 210. More specifically, the warning control ECU 110 increments an eye-closure counter value C (initial value: 0) when a eye-closure trigger is input in a determination period, and increments the eye-closure counter value C every time a eye-closure trigger is input in the subsequent determination periods. The warning control ECU 110 basically counts up the eye-closure triggers input in successive determination periods, but may have a filter for maintaining the eye-closure counter value C when a particular temporal discontinuity of eye-closure triggers occurs. The warning control ECU 110 calculates the period for which the eyes of the driver are closed, that is, the eye-closing period d [sec], by multiplying the eye-closure counter value C by the determination period $\Delta T$.

When the calculated eye-closing period d exceeds a predetermined threshold value $d_{Th}$ (hereinafter referred to as "first threshold value $d_{Th}$"), the warning control ECU 110 changes the pre-crash determination threshold value Th from the default value T0 to a value at which the PCS ECU 230 is more likely to detect a collision possibility. More specifically, the warning control ECU 110 changes the pre-crash determination threshold value Th to a value T1 (for example, T0+1.5 seconds), which is greater than the default value T0. The first threshold value $d_{Th}$ may be an appropriate value in the range of 1 to 3 seconds, for example.

Thus, in this embodiment, since the pre-crash determination threshold value T is increased from T0 to T1 when the period for which the driver's eyes are closed exceeds the first threshold value $d_{Th}$, the period which it takes for the inter-vehicular time to fall below the pre-crash determination threshold value Th becomes shorter accordingly. That is, an early-warning mode in which the timing of output of a warning is advanced from that used in the normal mode is established. Even when the early-warning mode is established, no collision warning is output unless the PCS ECU 230 detects a collision possibility.

When the early-warning mode is established, a collision warning is output sooner than in the normal mode. Thus, when the PCS ECU 230 actually detects a collision possibility and a collision warning is output, even if it takes some time for the driver to be awakened by the collision warning, the driver may have sufficient time to take appropriate evasive action to avoid the collision possibility after being awakened.

The warning control ECU 110 also calculates the maximum eye-closing period ld [sec] within the period between the current time and a period $\Delta Tw$ before the current time (hereinafter referred to simply as "maximum eye-closing period ld") using a time window with a predetermined duration $\Delta Tw$ based on the time sequence of the eye-closing period d calculated as described above. As the duration $\Delta Tw$, an appropriate value in the range of 5 to 35 [sec], for example, may be used.

When the calculated maximum eye-closing period ld falls below a predetermined threshold value $ld_{Th}$ (hereinafter referred to as "second threshold value $ld_{Th}$"), the warning control ECU 110 changes the pre-crash determination threshold value Th to the default value T0 or maintains the pre-crash determination threshold value Th at the default value T0. The second threshold value $ld_{Th}$ is a value greater than 0 and smaller than the first threshold value $d_{Th}$, and may be 1 [sec], for example.

Thus, in this embodiment, when the eye-closing period d of the driver exceeds the first threshold value $d_{Th}$ and the early-warning mode is established, the early-warning mode is maintained until the maximum eye-closing period ld falls below the threshold value $ld_{Th}$. Then, only if the maximum eye-closing period ld falls below the predetermined threshold value $ld_{Th}$, the pre-crash determination threshold value Th is returned to the default value T0. That is, the operation is restored from the early-warning mode to the normal mode.

Figure 2:
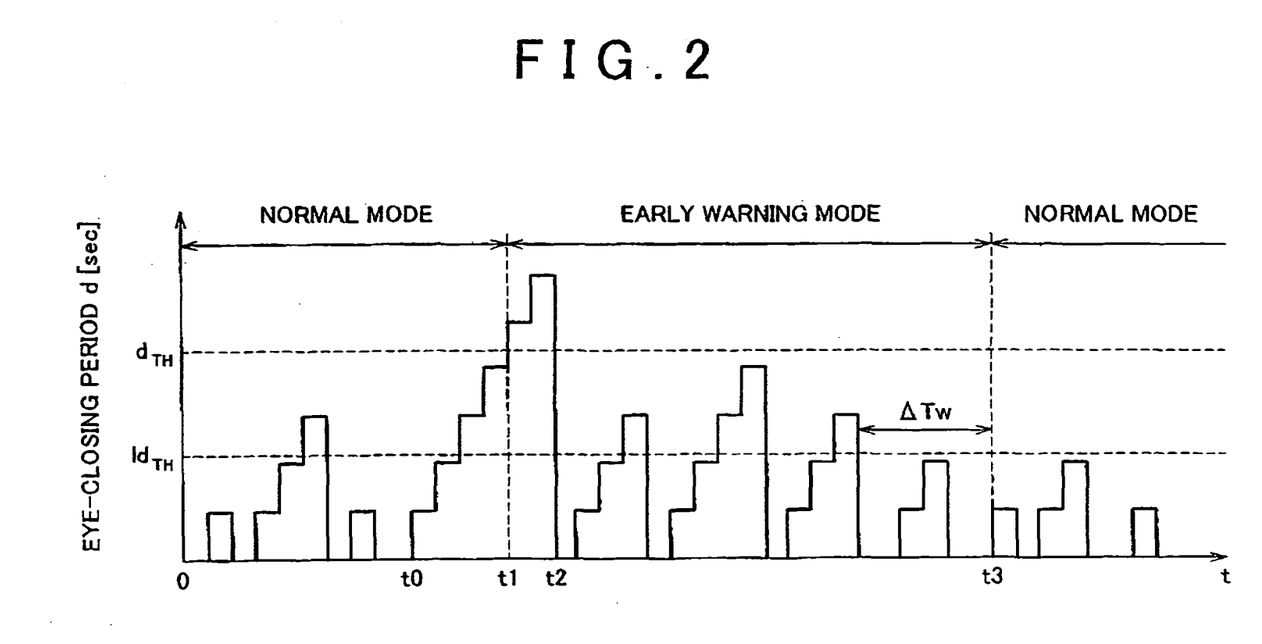
FIG. 2 is a chart showing an example of the time sequence of the eye-closing period d and a manner of switching between an early-warning mode and a normal mode, which are implemented in this embodiment.

FIG. 2 is a chart showing an example of the time sequence of the eye-closing period d and a manner of switching between an early-warning mode and a normal mode which is implemented in this embodiment.

In the example shown in FIG. 2, the eye-closing period d continuing from a time t0 (the eye-closing period d at the third eye closure since the start of measurement) exceeds the first threshold value $d_{Th}$ and the operation is shifted from the normal mode to the early-warning mode at a time t=t1. In this example, since the eye-closing period d falls below the first threshold value $d_{Th}$ at a time t=t2 after the time t=t1 but the maximum eye-closing period ld does not fall below the second threshold value $ld_{Th}$ until a time t=t3, the early-warning mode is maintained until the time t=t3. At the time t=t3, the maximum eye-closing period ld falls below the second threshold value $ld_{Th}$ and the operation is returned from the early-warning mode to the normal mode.

As described above, according to this embodiment, once a situation in which the eye-closing period d exceeds the first threshold value $d_{Th}$ is detected, even if the eye-closing period d falls below the first threshold value $d_{Th}$ (that is, the eyes are opened) thereafter, it is determined that the driver may be struggling to keep his or her eyes open against heavy drowsiness (the driver may have not returned to the normal awakened state), and the early-warning mode is maintained unless the maximum eye-closing period ld falls below the second threshold value $ld_{Th}$. Therefore, the possibility of returning from the early-warning mode to the normal mode while the driver is still feeling drowsy can be reduced effectively.

Also, according to this embodiment, since the operation is returned from the early-warning mode to the normal mode when a situation in which the eye-closing period d exceeds the first threshold value $d_{Th}$ is detected and then the maximum eye-closing period ld falls below the second threshold value $ld_{Th}$, it is possible to prevent the early-warning mode from being unnecessarily maintained. That is, according to this embodiment, since it is determined that the driver has returned to the normal awakened state and the operation is returned to the early-warning mode to the normal mode when the maximum eye-closing period ld falls below the second threshold value $ld_{Th}$, the possibility of the early-warning mode being established while the driver is in the normal awakened state can be reduced effectively.

Figure 3:
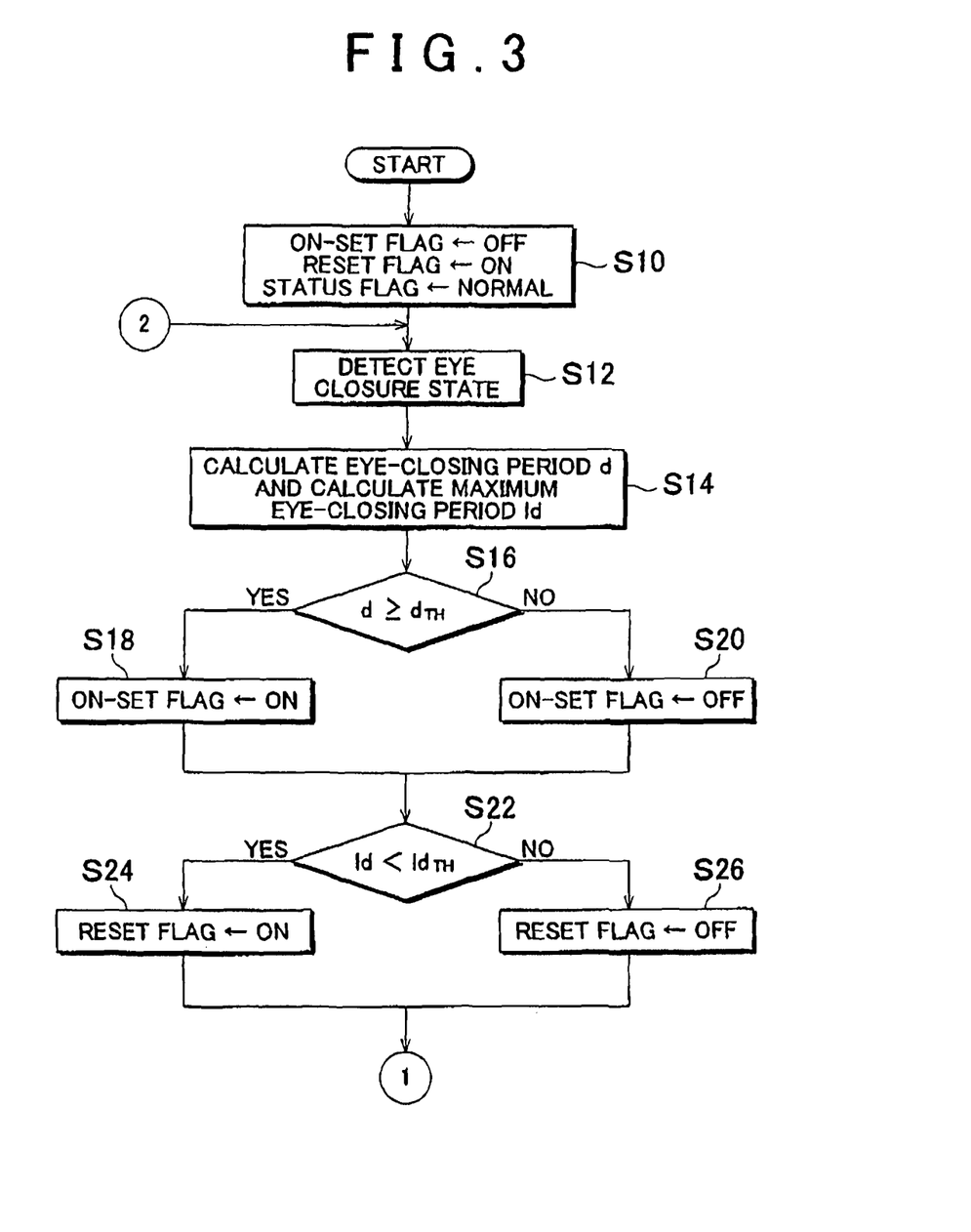
FIG. 3 is a first half of a flowchart illustrating a specific example of the primary operation of a warning control ECU 110.
Figure 4:
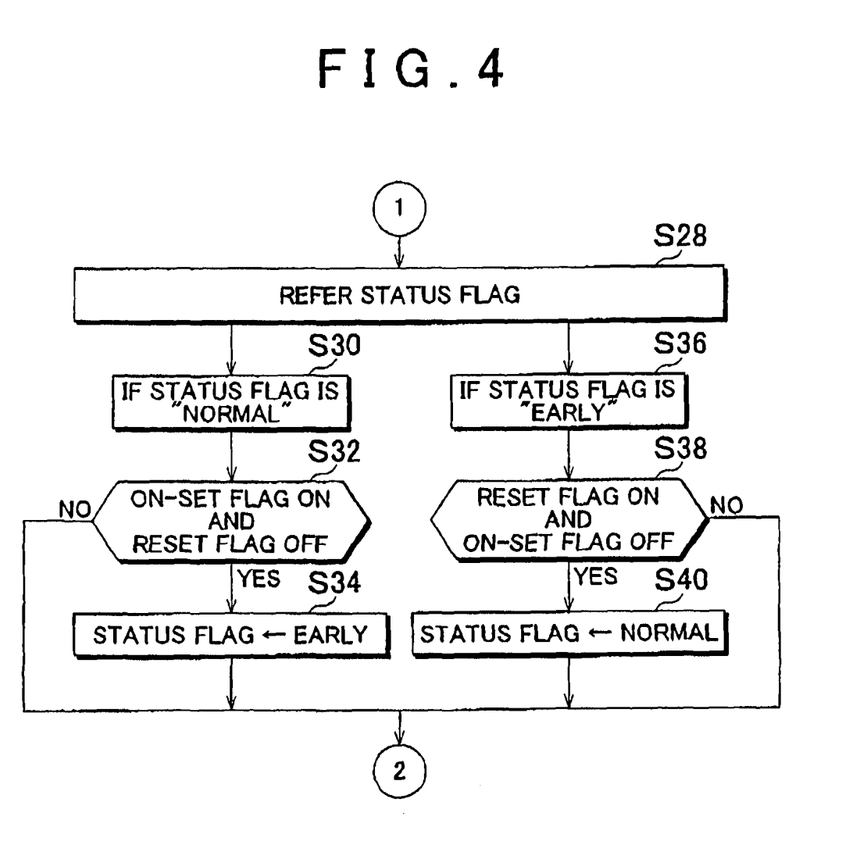
FIG. 4 is a second half of a flowchart illustrating a specific example of the primary operation of a warning control ECU 110.

A specific example of the primary operation of the warning control ECU 110 of this embodiment is next described with reference to the flowcharts of FIG. 3 and FIG. 4. The operation shown in FIG. 3 and FIG. 4 is repeated at a constant frequency (typically, in each determination period ΔT of the driver monitor ECU 210) until the ignition switch of the vehicle is turned off after it is turned on. Also, the operation shown in FIG. 3 and FIG. 4 is performed while the output state of the collision warning from the PCS ECU 230 is in the OFF state. This is because the mode switching between the early-warning mode and the normal mode while the output state of the collision warning in the ON state, that is, while the PCS ECU 230 is outputting a collision warning, is useless.

In step 10, the warning control ECU 110 initializes flags. Here, three flags, an ON-set flag, a reset flag and a status flag, are used, and the ON-set flag is set to OFF, the reset flag to ON and the status flag is to "normal" by the initialization. In reality, however, the state of each flag may be represented by binary values "0" and "1". The warning control ECU 110 also initializes the eye-closure counter value C to 0. The process in step 10 is performed only in the first cycle.

In the following step 12, the warning control ECU 110 achieves information representing the latest eye closure state of the driver. More specifically, the warning control ECU 110 checks the presence or absence of an input of an eye-closure trigger from the driver monitor ECU 210 in the current cycle.

In the following step 14, the warning control ECU 110 calculates the eye-closing period d depending on the presence or absence of an input of an eye-closure trigger from the driver monitor ECU 210 in the current cycle. Then, the maximum eye-closing period ld is calculated based on the time sequence of the calculated eye-closing period d. More specifically, when an eye-closure trigger is input from the driver monitor ECU 210 in the current cycle, the warning control ECU 110 increments the eye-closure counter value C, and calculates an eye-closing period d(i) in the current cycle (i) based on the thus obtained eye-closure counter value C. When no eye-closure trigger has been inputted from the driver monitor ECU 210 in the current cycle, the warning control ECU 110 sets the eye-closing period d(i) in the current cycle to 0 and stores it in memory (not shown). In this way, the time sequence of the eye-closing period d calculated in each cycle is stored and accumulated in the memory. The warning control ECU 110 calculates (extracts) the maximum value of the eye-closing period d in the cycles within the period between the current time and a time prior to the current time by the duration ΔT as the maximum eye-closing period ld(i) in the current cycle (i) based on the time sequence of the eye-closing period d in the memory.

In the following step 16, the warning control ECU 110 determines whether or not the eye-closing period d(i) in the current cycle (i) obtained in the above step 14 is greater than the first threshold value $d_{Th}$. If the eye-closing period d(i) in the current cycle (i) is greater than the first threshold value $d_{Th}$, the process goes to step 18; otherwise the process goes to step 20.

In step 18, the warning control ECU 110 sets the ON-set flag to ON. Then, the process goes to step 22.

In step 20, the warning control ECU 110 sets the ON-set flag to OFF. Then, the process goes to step 22.

In step 22, the warning control ECU 110 determines whether or not the maximum eye-closing period ld(i) in the current cycle (i) obtained in the above step 14 is smaller than the second threshold value $ld_{Th}$. If the maximum eye-closing period ld(i) in the current cycle (i) is smaller than the second threshold value $ld_{Th}$, the process goes to step 24; otherwise the process goes to step 26.

In step 24, the warning control ECU 110 sets the reset flag to ON. Then, the process goes to step 28 in FIG. 4.

In step 26, the warning control ECU 110 sets the reset flag to OFF. Then, the process goes to step 28.

In step 28, the warning control ECU 110 refers to the current state of the status flag. If the status flag is "normal" in the current cycle (i) (step 30), the process goes to step 32. If the status flag is "early" in the current cycle (i) (step 36), the process goes to step 38.

In step 32, the warning control ECU 110 determines whether or not the ON-set flag is ON and whether or not the reset flag is OFF. If the ON-set flag is ON and the reset flag is OFF, the process goes to step 34. If either of the conditions is not satisfied, the process returns to step 12 in FIG. 3. Then, the operation is repeated from step 12 in the next cycle (i+1).

In step 34, the warning control ECU 110 sets the status flag to "early." Along with this, the pre-crash determination threshold value Th is set to a value T1 which is greater than the default value T0, and the PCS ECU 230 operates in the early-warning mode using the value T1.

In step 38, the warning control ECU 110 determines whether or not the reset flag is ON and whether or not the ON-set flag is OFF. If the reset flag is ON and the ON-set flag is OFF, the process goes to step 40. If either of the conditions is not satisfied, the process returns to step 12 in FIG. 3. Then, the operation is repeated from step 12 in the next cycle (i+1).

In step 40, the warning control ECU 110 sets the status flag to "normal." Along with this, the pre-crash determination threshold value Th is set to the default value T0, and the PCS ECU 230 operates in the normal mode using the default value T0.

The results of a test conducted using the anti-drowsing device of this embodiment is next described.

Here, the usefulness of the anti-drowsing device of this embodiment is described by comparison with a comparative example. In the comparative example, the normal mode and the early-warning mode are switched based an index value P called PERCLOS. That is, the early-warning mode is established when the index value P exceeds a predetermined threshold value (0.08 in this example) and the normal mode is established when the index value P falls below the predetermined threshold value. The index value P is represented by the following equation:

$$P = \frac{\sum_{i=1}^{N} d_i}{w_P}$$

In the equation, $d_i$ represents the eye-closing period d at the i-th eye closure, and $w_P$ represents the duration of the time window, which is 60 [sec] here. Therefore, the index value P is a value obtained by dividing the summation of the eye-closing periods d within a period between the current time and 60 seconds before the current time by $w_P$, that is, the ratio of the eye-closing period per unit time.

Figure 5A:
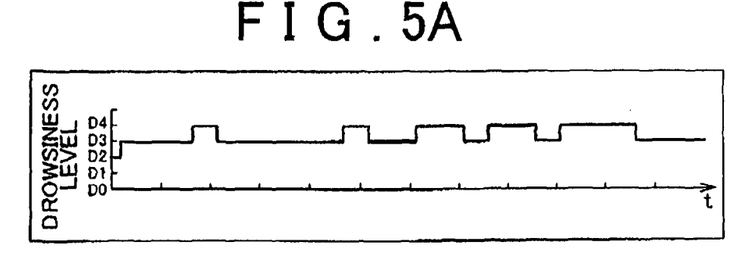
FIGS. 5A, 5B, 5C and 5D are charts showing the data of the results of a test in time sequence.

FIG. 5(A) shows the change in drowsiness level of a subject during the test. Here, the drowsiness level is rated on a five-point scale of D0 to D4. The drowsiness level D0 represents the normal state in which the driver is awake, the drowsiness level D2 represents the state in which the driver is feeling a little drowsy, and the drowsiness level D4 represents the state in which the driver is feeling very drowsy. Here, the ideal test result is that the early-warning mode is established when the drowsiness level is D3 or D4 (D4, in particular) and the normal mode is established when the drowsiness level is lower than D3. The test result shown in FIG. 5(A) was the result of a test (sensory evaluation test) conducted with understanding the alertness level (drowsiness level) of the subject, and indicates that the drowsiness level of the subject constantly remained at D3 or D4 throughout the test.

Figure 5B:
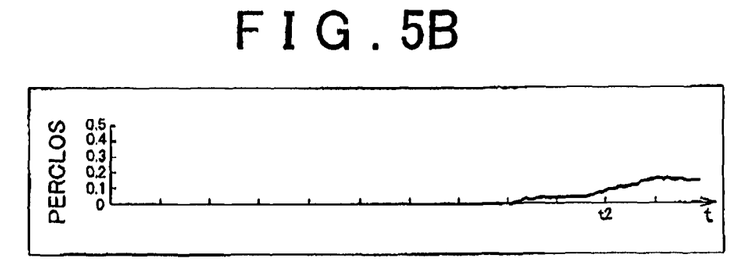
Figure 5C:
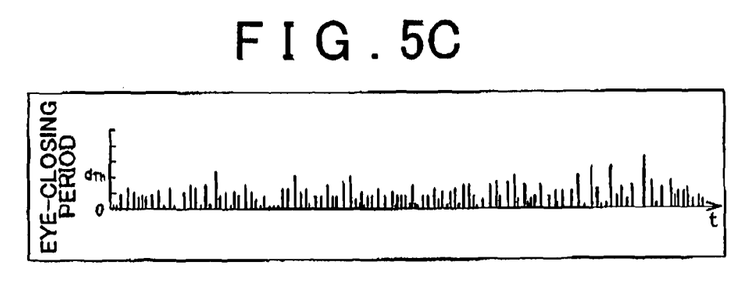
Figure 5D:
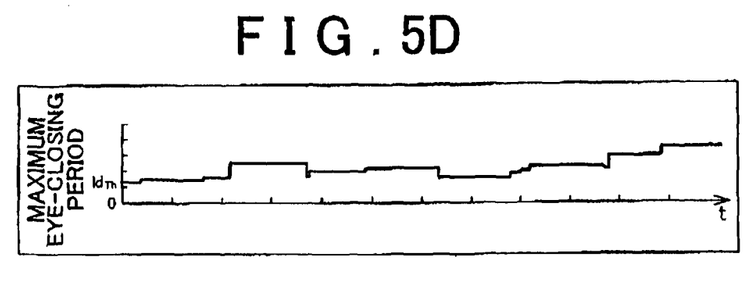

FIG. 5(B) shows the time sequence of the index value P (PERCLOS) during the test, FIG. 5(C) shows the time sequence of the eye-closing period d during the test, and FIG. 5(D) shows the time sequence of the maximum eye-closing period ld during the test. In FIG. 5(C), the eye-closing period d at each eye closure is shown in time sequence because of the scale of the horizontal axis. Also, the maximum eye-closing period ld was calculated using a time window with a relatively long duration ΔTw (30 sec in this example).

Figure 6A:
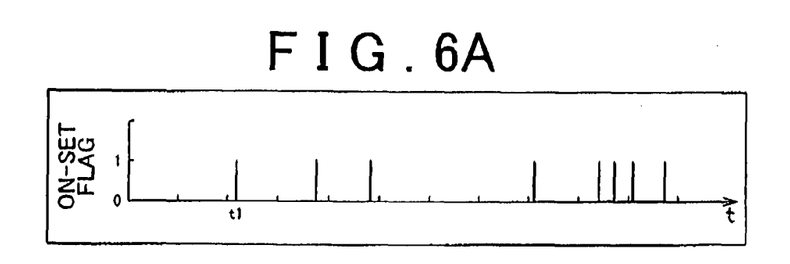
FIGS. 6A, 6B, 6C, 6D and 6E are charts showing the data of the results of a test in time sequence.
Figure 6B:
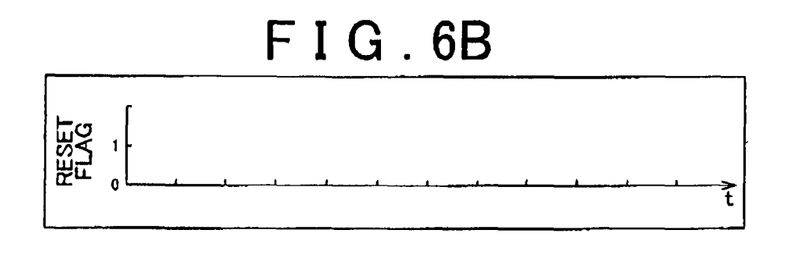
Figure 6C:
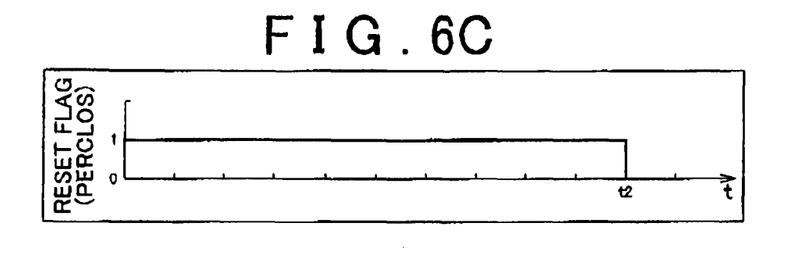
Figure 6D:
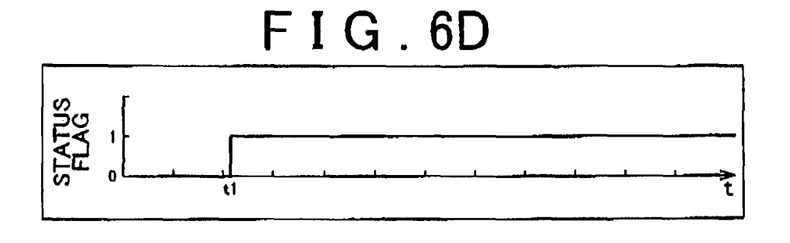
Figure 6E:
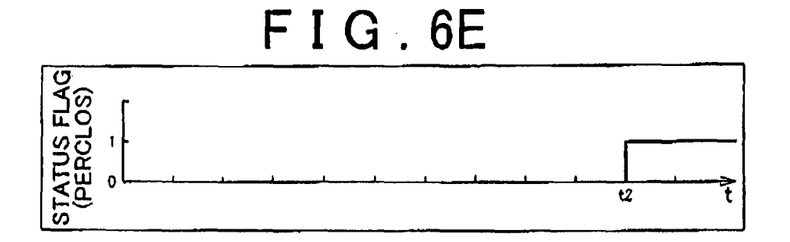

FIG. 6(A) shows the time sequence of the state of the ON-set flag of this embodiment during the test, FIG. 6(B) shows the time sequence of the state of the reset flag of this embodiment during the test, FIG. 6(C) shows the time sequence of the state of the reset flag according to the comparative example during the test, FIG. 6(D) shows the time sequence of the state of the status flag of this embodiment during the test, and FIG. 6(E) shows the time sequence of the state of the status flag according to the comparative example during the test. The reset flag of the comparative example is set to "0" when the index value P exceeds a predetermined threshold value (0.08 in this example) and set to "1" when the index value P falls below the predetermined threshold value. The status flag of the comparative example varies depending on the state of the reset flag, and is set to "1" when the reset flag is set to "0." When the status flag is set to "1," the early-warning mode is established.

In this embodiment, the ON-set flag was turned ON (that is, the ON-set flag was changes from 0 to 1) for the first time at a time t=t1 when the eye-closing period d exceeded the first threshold value $d_{Th}$, and after that the ON-set flag was turned ON seven times in total in the same manner as shown in FIG. 5(C) and FIG. 6(A). The reset flag was maintained in OFF state since the maximum eye-closing period ld was greater than the second threshold value $ld_{Th}$ throughout the test as shown in FIG. 5(D) and FIG. 6(B). Therefore, the status flag was set to "early" (that is, value 1) at the time t=t1 in response to the turn-ON of the ON-set flag at the time t=t1 and maintained at "early" thereafter as shown in FIG. 6(D). Thus, the early-warning mode was continuously maintained from the time t=t1 in this embodiment.

In the comparative example, the reset flag was set to "0" at time t2 when the index value P exceeded a predetermined threshold value as shown in FIG. 5(B) and FIG. 6(C). After that, the reset flag was maintained at "0" since the index value P remained higher than the predetermined threshold value. Therefore, the status flag was set to "early" (that is, value 1) at the time t=t2 in response to the turn-ON of the ON-set flag at the time t=t2 and maintained at "early" thereafter as shown in FIG. 6(E). Thus, the early-warning mode was continuously maintained from the time t=t2 in the comparative example.

Figure 7A:
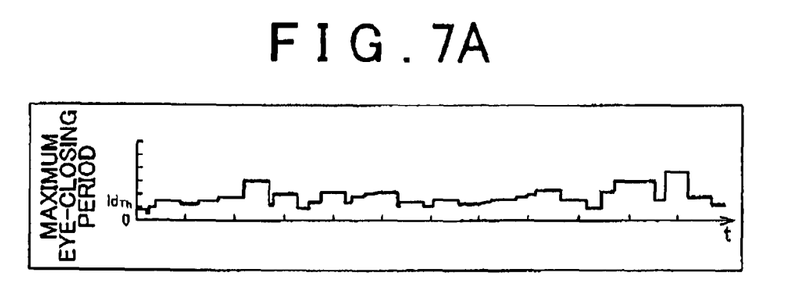
FIGS. 7A, 7B and 7C are charts showing the data of the results of a test in time sequence.
Figure 7B:
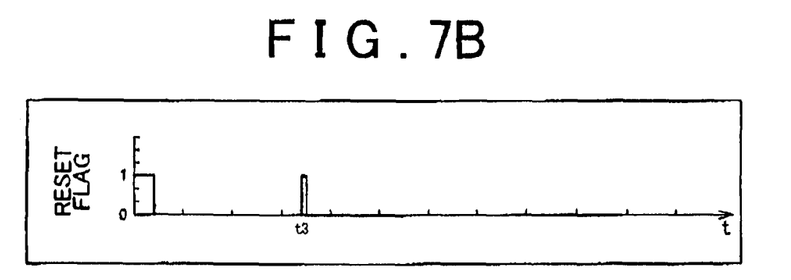
Figure 7C:
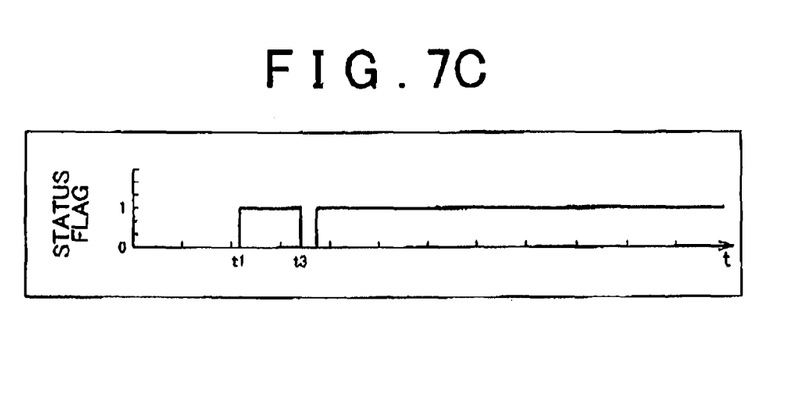

FIG. 7 shows the results of a test conducted using a time window with a relatively short duration ΔTw (in this example, 10 sec). FIG. 7(A) shows the time sequence of the maximum eye-closing period ld during the test, FIG. 7(B) shows the time sequence of the state of the reset flag of this embodiment during the test, and FIG. 7(C) shows the time sequence of the state of the status flag of this embodiment during the test. The other tests results are the same as those in FIG. 5(A), FIG. 5(C) and FIG. 6(A).

When the duration ΔTw was set short, the reset flag was turned ON at a time t=t3 when the maximum eye-closing period ld fell below the second threshold value $ld_{Th}$ as shown in FIG. 7(A) and FIG. 7(B). The status flag was set to "early" (that is, value 1) at a time t=t1 in response to the turn-ON of the ON-set flag at the time t=t1 and then set to "normal" (that is, value 0) at the time t=t3 in response to the turn-ON of the reset flag at the time t=t3 as shown in FIG. 7(C). Therefore, when a time window with a relatively short duration ΔTw (in this example, 10 sec) was used, the early-warning mode was established at the time t=t1 and the operation was returned to the normal mode at the time t=t3 in this embodiment.

As can be understood from the test results, according to this embodiment, whether the duration ΔTw was long or short, the early-warning mode was able to be established according to the drowsiness level of D3 to D4 with high accuracy as compared to the comparative example.

Figure 10A:
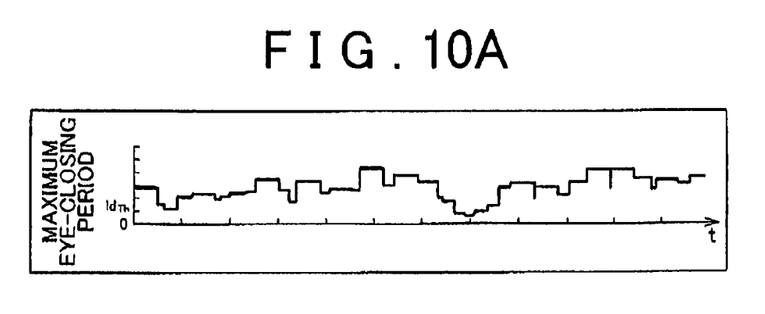
FIGS. 10A, 10B and 10C are charts showing the data of the results of a test in time sequence.
Figure 10B:
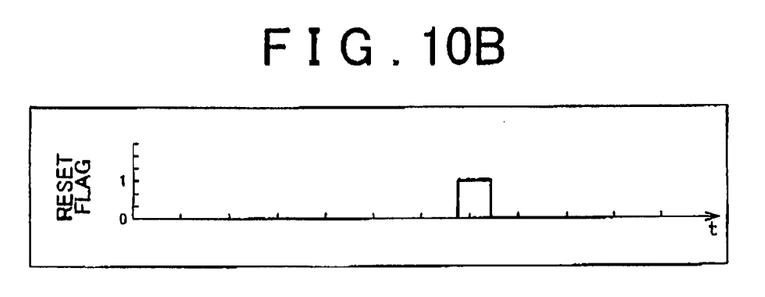

FIG. 8 to FIG. 10 shows the results of a test different from the test, the results of which are shown in FIG. 5 to FIG. 7. The charts of FIG. 8 respectively correspond to the charts of FIG.

5, the charts of FIG. 9 respectively correspond to the charts of FIG. 6, and the charts of FIG. 10 respectively correspond to the charts of FIG. 7.

Figure 8A:
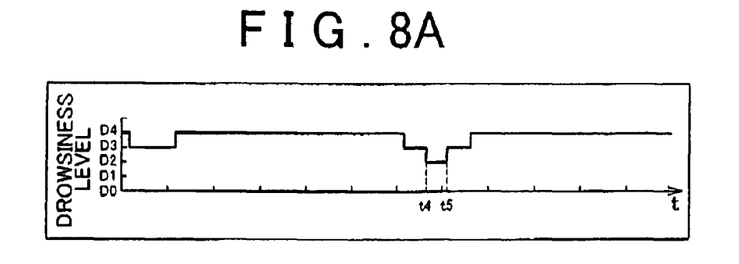
FIGS. 8A, 8B, 8C and 8D are charts showing the data of the results of a test in time sequence.
Figure 8B:
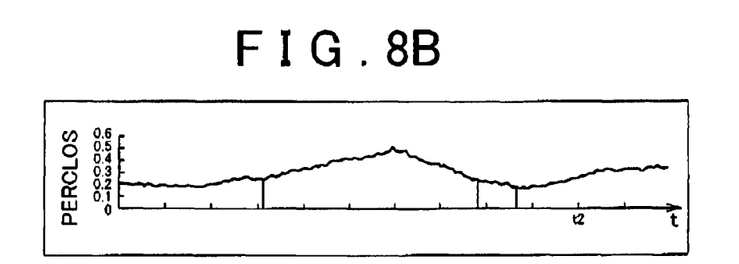
Figure 8C:
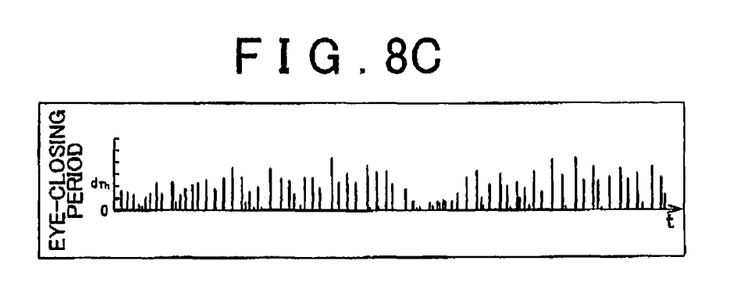
Figure 8D:
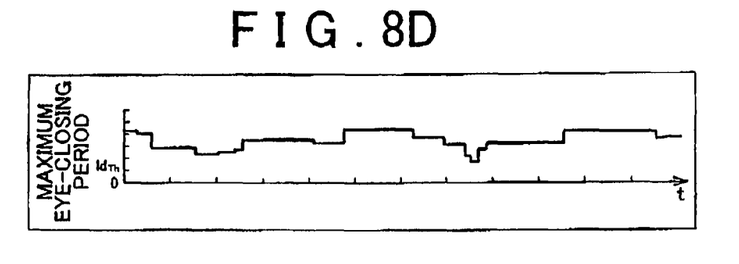

In this test, the drowsiness level of the subject constantly remained at D3 or D4 throughout the test except for the period from a time t=t4 to a time t=t5, in which the drowsiness level was lowered to D2 as shown in FIG. 8(A).

Figure 9A:
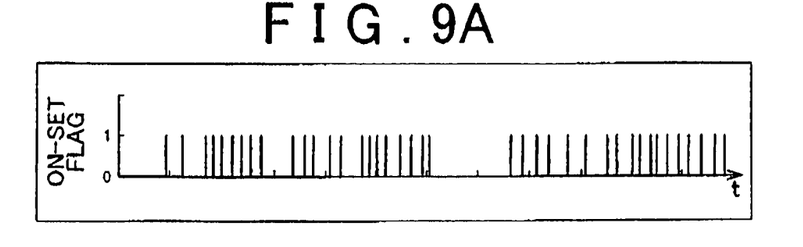
FIGS. 9A, 9B, 9C, 9D and 9E are charts showing the data of the results of a test in time sequence.
Figure 9B:
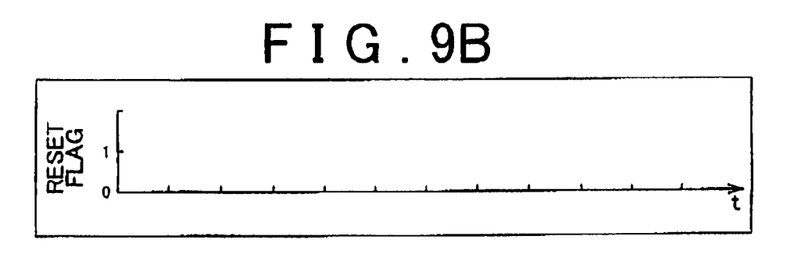
Figure 9C:
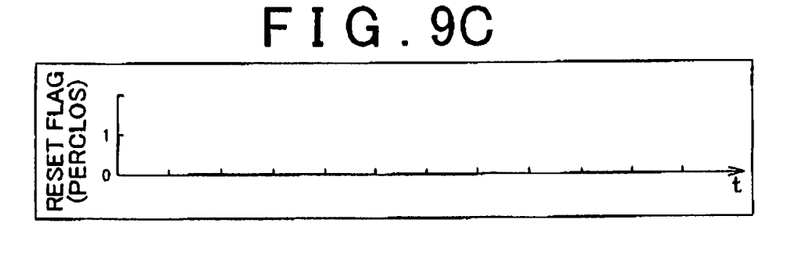
Figure 9D:
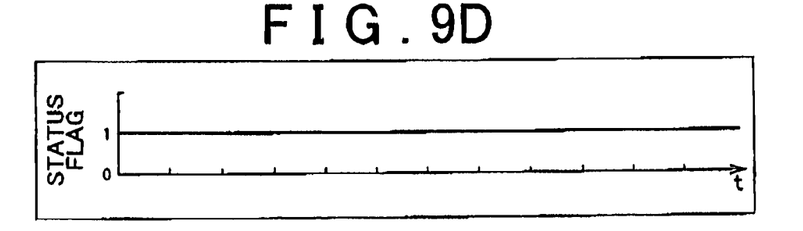
Figure 9E:
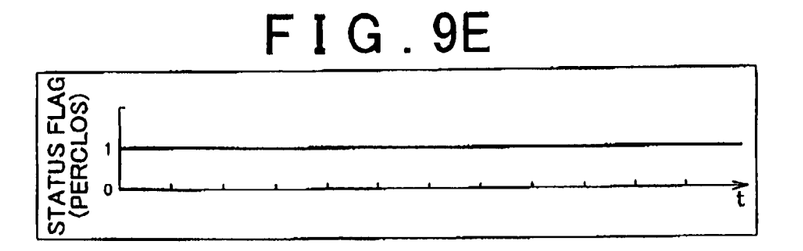
Figure 10C:
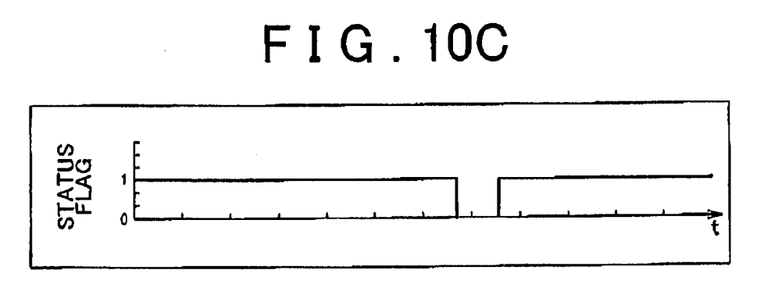

As can be understood from the results of this test, according to this embodiment, when the duration ΔTw was set long, the early-warning mode was established according to the drowsiness level of D3 to D4 accurately although the operation was not able to be returned to the normal mode in the period from the time t=t4 to the time t=t5 as shown in FIG. 9(D). When the duration ΔTw was set short, the early-warning mode was established according to the drowsiness level of D3 to D4 accurately and the normal mode was established according to the drowsiness level of D2 accurately as shown in FIG. 10(C).

Figure 11:
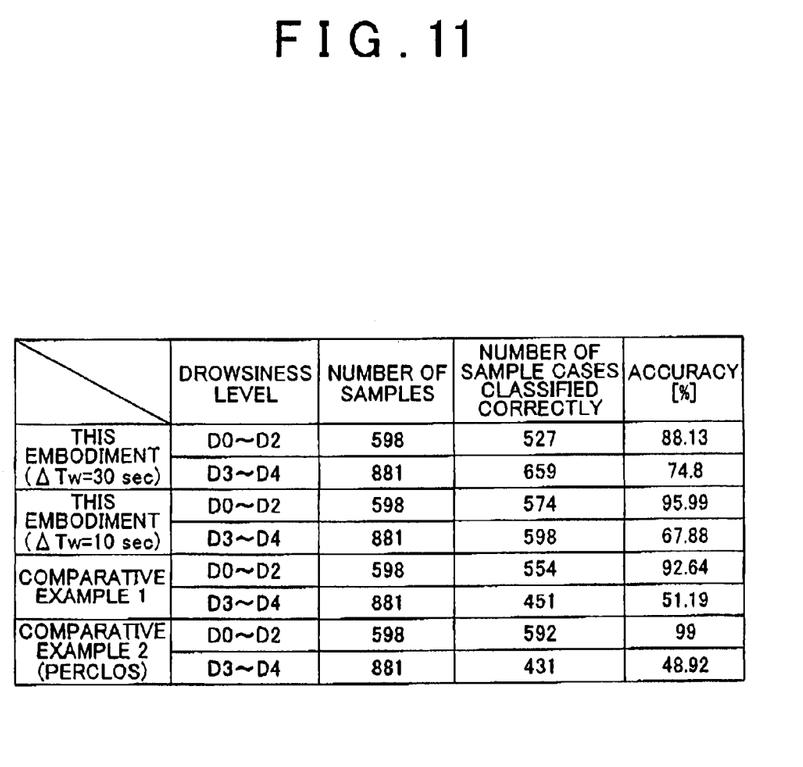
FIG. 11 is a table summarizing the test results.

FIG. 11 shows a table summarizing the results of the tests shown in FIG. 5 to FIG. 10. In FIG. 11, "Number of sample cases" represents the number of sample cases in which the consistency between the sensory test and the test results was observed. In the tests, there were 598 sample cases in the drowsiness levels of D0 to D2, and there were 881 sample cases in the drowsiness levels of D3 and D4.

The uppermost row of FIG. 11 shows the test results obtained when the duration ΔTw was set long in this embodiment. When the duration ΔTw was set long in this embodiment, the fact that the drowsiness level was in the range of D0 to D2 was able to be estimated with an accuracy of 527/598 (=88.13%) and the fact that the drowsiness level was in the range of D3 to D4 was able to be estimated with an accuracy of 659/881 (=74.8%).

The second row from the top in FIG. 11 shows the test results obtained when the duration ΔTw was set short in this embodiment. When the duration ΔTw was set short in this embodiment, the fact that the drowsiness level was in the range of D0 to D2 was able to be estimated with an accuracy of 574/598 (=95.99%) and the fact that the drowsiness level was in the range of D3 to D4 was able to be estimated with an accuracy of 598/881 (=67.88%).

The third row from the top in FIG. 11 shows the test results in Comparative Example 1. In Comparative Example 1, it was determined that the drowsiness level was in the range of D3 to D4 and the early-warning mode was established when the eye-closing period d exceeded the first threshold value $d_{Th}$, and it was determined that the drowsiness level was in the range of D0 to D2 and the normal mode was established when the eye-closing period d fell below the first threshold value $d_{Th}$. In Comparative Example 1, the fact that the drowsiness level was in the range of D0 to D2 was able to be estimated with an accuracy of 554/598 (=92.64%) whereas the fact that the drowsiness level was in the range of D3 to D4 was able to be estimated with only an accuracy of slightly higher than 50%, which is 451/881 (=51.19%).

The fourth row from the top (lowermost row) in FIG. 11 shows the test results in Comparative Example 2. In Comparative Example 2, it was determined that the drowsiness level was in the range of D3 to D4 and the early-warning mode was established when the index value P (PERCLOS) exceeded a predetermined threshold value (in this example 0.08), and it was determined that the drowsiness level was in the range of D0 to D2 and the normal mode was established when the index value P fell below the predetermined threshold value. In Comparative Example 2, the fact that the drowsiness level was in the range of D0 to D2 was able to be estimated with a high accuracy of 592/598 (=99%) whereas the fact that the drowsiness level is in the range of D3 to D4 was able to be estimated with only an accuracy of lower than 50%, which is 431/881 (=48.92%).

As can be understood from the summary of test results shown in FIG. 11, according to this embodiment, the fact that the drowsiness level is in the range of D3 to D4 can be estimated and the early-warning mode can be established accurately as compared to Comparative Examples 1 and 2. In this embodiment, the accuracy in the drowsiness level of D3 to D4 is 67.88%, which is higher than two-thirds, even when the duration ΔTw is set short. When the duration ΔTw is set long, the accuracy is 74.8%, which is much higher than those in other examples. In addition, according to this embodiment, the normal mode can be also established according to the drowsiness level of D0 to D2 with high accuracy. In this embodiment, when the duration ΔTw is set short, the accuracy in the drowsiness level of D3 to D4 is as very high as 95.99%. Even when the duration ΔTw is set long, the accuracy is maintained at as high as 88.13%.

As described above, according to this embodiment, once the eye-closing period d exceeds the first threshold value $d_{Th}$, it is thereafter determined that the drowsiness level is in the range of D3 to D4 until the maximum eye-closing period ld falls below the second threshold value $ld_{Th}$. Therefore, both the accuracy in the drowsiness level of D0 to D2 and the accuracy in the drowsiness level of D3 to D4 can be enhanced. As a result, the early-warning mode and the normal mode can be switched depending on the actual drowsiness level of the driver with high accuracy.

As can be understood from the summary of the test results in FIG. 11, when the method of calculating the maximum eye-closing period ld is different (that is, the duration ΔTw of the time window is changed), the accuracy in the drowsiness level of D0 to D2 and the accuracy in the drowsiness level of D3 to D4 varies significantly while still remaining high. Therefore, in this embodiment, it is useful to change the duration ΔTw of the time window depending on the running condition of the vehicle, the condition of the driver, the condition of the surrounding environment, or the like.

For example, in this embodiment, the warning control ECU 110 may set the duration ΔTw of the time window to a large value (for example, 30 sec) when it is determined that the vehicle is running on an expressway and set the duration ΔTw of the time window to a small value (for example, 10 sec) when it is determined that the vehicle is running on an ordinary road based on information on the location of the vehicle and map information from a navigation ECU 290, for example. This is because driving on an expressway tends to be monotonous than driving on an ordinary road and drowsiness is likely to continue accordingly. In this case, the type of the road on which the vehicle is running may be determined based on information based on the result of image recognition of the surrounding environment using an onboard camera (not shown) or information obtained through road-to-vehicle communication instead of information from the navigation ECU 290. Also, the fact that the vehicle is driving on an expressway may be determined based on information from a sensor for detecting the vehicle speed such as the wheel speed sensor 270. For example, since the legal speed limit on expressways is usually 80 km/h in Japan, the duration ΔTw of the time window may be set to a large value (for example, 30 sec) when the vehicle speed exceeds 70 km/h and set to a small value (for example, 10 sec) when the vehicle speed falls below 70 km/h.

In this embodiment, the "warning output means" may be implemented cooperatively by the PCS ECU 230 and the buzzer 240, the "eye-closing period measurement means"

may be implemented cooperatively by the driver monitor camera 212, the driver monitor ECU 210 and the warning control ECU 110, and the "warning timing change means" may be implemented by the warning control ECU 110. The "predetermined period" may correspond to the duration ΔTw.

While a preferred embodiment of the present invention has been described, the present invention is not limited to the embodiment and various changes and modifications may be made thereto without departing from the scope of the present invention.

For example, while the early-warning mode is established when the eye-closing period d exceeds the first threshold value $d_{Th}$, and the early-warning mode is thereafter maintained until the maximum eye-closing period ld falls below the second threshold value $ld_{Th}$ in the above embodiment, the present invention is not limited thereto. Another index value capable of representing the degree of drowsiness of the driver may be used instead of the eye-closing period d. That is, the early-warning mode may be established when the other index value exceeds a predetermined threshold value Th2, and the early-warning mode may be thereafter maintained until the maximum eye-closing period ld falls below the second threshold value $ld_{Th}$. In this case, as the other index value, the summation of the eye-closing periods within a predetermined period between the current time and a predetermined time before the current time, the ratio of the summation to the predetermined period (which corresponds to the PERCLOS described before), or the number of times the eye-closing period exceeding a predetermined threshold value within a predetermined period between the current time and a predetermined time before the current time (for example, the frequency at which the eye-closing period d exceeds the first threshold value $d_{Th}$ per a given period) may be used. In this case, however, the predetermined threshold value Th2 for the other index value is set to a value with which a substantially higher drowsiness level can be detected than when using with the second threshold value $ld_{Th}$ for the maximum eye-closing period ld.

Also, while the early-warning mode is established when the eye-closing period d exceeds the first threshold value $d_{Th}$, and the early-warning mode is thereafter maintained until the maximum eye-closing period ld falls below the second threshold value $ld_{Th}$ in the above embodiment, the present invention is not limited thereto. Another index value capable of representing the degree of drowsiness of the driver may be used instead of the maximum eye-closing period ld. That is, the early-warning mode may be established when the eye-closing period d exceeds the first threshold value $d_{Th}$ and the early-warning mode may be thereafter maintained until the other index value falls below a predetermined threshold value Th3. In this case, as the other index value, the summation of the eye-closing periods within a predetermined period between the current time and a predetermined time before the current time, the ratio of the summation to the predetermined period (which corresponds to the PERCLOS described before), or the number of times the eye-closing period exceeding a predetermined threshold value within a predetermined period between the current time and a predetermined time before the current time (for example, the frequency at which the eye-closing period d exceeds the first threshold value $d_{Th}$ per a given period) may be used. In this case, however, the predetermined threshold value Th3 for the other index value is set to a value with which a substantially lower drowsiness level can be detected than when using with the first threshold value $d_{Th}$ for the eye-closing period d.

While only index values relating to the eye-closing period are used as the index values capable of representing the degree of drowsiness of the driver to implement a simple configuration in the above example, index values relating to a physiological feature quantity such as the number of yarns, brain waves, or heart rate may be used as additional conditions to establish the early-warning mode or to restore to the normal mode.

While a collision possibility is detected based simply on the relation between the inter-vehicular time and the predetermined threshold value Th in the above embodiment, for example, a collision possibility may be detected using another method. For example, a collision possibility may be detected using a two-dimensional map defined by the inter-vehicular distance between a preceding object and the host vehicle and the speed of the host vehicle relative to the preceding object. In this case, a threshold value curve dividing a high collision risk region and a low collision risk region may be defined on the two-dimensional map, for example, and a collision possibility may be determined when the detected current inter-vehicular distance and relative speed fall within the high collision risk region divided by the threshold value curve. In this case, the early-warning mode may be established by shifting the threshold value curve for the normal mode in such a way that the sensitivity increases (the high collision risk region is enlarged). Also, a collision possibility may be detected using other physical quantities such as acceleration (deceleration) instead of the inter-vehicular distance and relative speed.

While the information representing the relative relation between a preceding object and the host vehicle is obtained from the radar sensor 280 in the above embodiment, when the preceding object has an interactive communication device, information of that kind may be obtained through communication (for example, inter-vehicular communication) therewith.

The invention claimed is:

1. An anti-drowsing device comprising:
a warning output device that outputs a warning when a collision possibility is detected between a preceding object and the vehicle;
a warning timing change device that establishes an early-warning mode in which the timing of output of a warning by the warning output device is advanced from that used in a normal mode; and
an eye-closing period measurement device that monitors the state of the driver's eyes and measures the period during which the driver's eyes are closed,
wherein the warning timing change device establishes the early-warning mode when the eye-closing period measured by the eye-closing period measurement device becomes equal to or greater than a first threshold value, and thereafter maintains the early-warning mode until the eye-closing period falls below a second threshold value which is smaller than the first threshold value.

2. The anti-drowsing device according to claim 1, wherein the subsequent eye-closing period is the maximum value of the eye-closing period measured by the eye-closing period measurement device within a predetermined period.

3. The anti-drowsing device according to claim 2, wherein the predetermined period is variable, and the predetermined period used when the vehicle is traveling on an expressway is longer than the predetermined period used when the vehicle is running on an ordinary road.

4. An anti-drowsing method for changing the timing of output of a warning, which is output when a collision possibility is detected between a preceding object and the vehicle, comprising:

monitoring the state of the driver's eyes and outputting a first index value that provides a temporal indication of the degree of drowsiness of the driver;

setting a first threshold value for the first index value;

establishing an early-warning mode, in which the timing of output of the warning is advanced from that used in a normal mode when the first index value exceeds the first threshold value;

monitoring the state of the driver's eyes and outputting a second index value that provides a temporal indication of the degree of drowsiness of the driver after the early-warning mode has been established;

setting a second threshold value which is smaller than the first threshold value for the second index value; and maintaining the early-warning mode until the second index value falls below the second threshold value.

5. The anti-drowsing method according to claim 4, wherein the first index value is the eye-closing period.

6. The anti-drowsing method according to claim 4, wherein the first index value is set based on the summation of the eye-closing periods over a predetermined period between the current time and a predetermined time before the current time.

7. The anti-drowsing method according to claim 4, wherein the first index value is the ratio of the summation to a predetermined period between the current time and a predetermined time before the current time.

8. The anti-drowsing method according to claim 4, wherein the first index value is the number of times the eye-closing period exceeds a predetermined threshold value within a predetermined period between the current time and a predetermined time before the current time.

9. The anti-drowsing method according to claim 4, wherein the second index value is the eye-closing period.

10. The anti-drowsing method according to claim 4, wherein the second index value is the summation of the eye-closing periods over a predetermined period between the current time and a predetermined time before the current time.

11. The anti-drowsing method according to claim 4, wherein the second index value is the ratio of the summation to a predetermined period between the current time and a predetermined time before the current time.

12. The anti-drowsing method according to claim 4, wherein the second index value is the number of times the eye-closing period exceeds a predetermined threshold value within a predetermined period between the current time and a predetermined time before the current time.

\* \* \* \* \*